United States Patent [19]

Colson et al.

[11] Patent Number: 4,806,426

[45] Date of Patent: Feb. 21, 1989

[54] MUTANT MICROORGANISMS CONTAINING RECOMBINANT DNA AND THEIR USE IN THE PRODUCTION OF AMYLASES

[75] Inventors: Charles A. Colson, Dion-Valmont; Philippe Lejeune, Verviers; Corinne Walon, Wavre; Karine Willemot, Charleroi, all of Belgium

[73] Assignee: CPC International Inc., Englewood Cliffs, N.J.

[21] Appl. No.: 737,311

[22] Filed: May 23, 1985

[30] Foreign Application Priority Data

Jun. 5, 1984 [GB] United Kingdom ............... 8414271

[51] Int. Cl.⁴ ............... C12N 1/20; C12N 15/00; C12N 9/28; C12R 1/125
[52] U.S. Cl. ............... 435/252.31; 435/172.1; 435/172.3; 435/202; 435/839; 935/74
[58] Field of Search ............... 435/172.3, 201, 202, 435/210, 320, 253, 832, 834, 837, 839, 852, 91, 172.1; 935/6, 14, 29, 60, 61, 74

[56] References Cited

U.S. PATENT DOCUMENTS

4,469,791 9/1984 Colson et al. ............... 435/253
4,598,048 7/1986 Diderichsen et al. ............... 435/172.3
4,626,510 12/1986 Grandi ............... 435/317

FOREIGN PATENT DOCUMENTS

0003062 7/1979 European Pat. Off. ............... 435/91
2091268 7/1982 United Kingdom ............... 435/172.3

OTHER PUBLICATIONS

Takeichi et al., "Cloning of *Bacillus subtilis* α-Amylase Structural Gene in Plasmid pUB110", *Agric. Biol. Chem.* vol. 47, No. 1, (1983); pp. 159–161.

Ortlepp et al., "Molecular Cloning in *Bacillus subtilis* of a *Bacillus licheniformis* Gene Encoding a Thermostable Alpha Amylase", *Gene*, vol. 23, (1983); pp. 267–276.

Yamazaki et al., "α-Amylase Genes (*amy* R2 and *dmyE*⁺) from an α-Amylase-Hyperproducing *Bacillus subtilis* Strain:Molecular Cloning and Nucleotide Sequences"; *J. Bacteriology*, vol. 156, No. 1, (Oct. 1983); pp. 327–337.

Lehtovaara et al., "*In vivo* Transcription Initiation and Termination Sites of an α-Amylase Gene from *Bacillus amyloliquefaciens* Cloned in *Bacillus subtilis*", *Gene*, vol. 30, (Oct. 1984), pp. 11–16.

Ohmura et al.; "A *Bacillus subtilis* Secretion Vector System Derived from the *B. subtilis* α-Amylase Promotor and Signal Sequence Region, and Secretion of *Escherichia coli* β-Lactamase by the Vector System"; *J. Biochem*, vol. 95 (1984); pp. 87–93.

Gryczan, et al., *J. Bacteriology*, 134, 318–329 (1978).
Palva, et al., *Gene*, 15, 43–51 (1981).
Palva, et al., *Gene*, 19, 81–87 (1982).
Stark, et al., *FEMS Microbiol. Lett.*, 15, 295–298 (1982).

*Primary Examiner*—Elizabeth C. Weimar

[57] ABSTRACT

Recombinant DNA containing amylase-coding genes is prepared by cleaving DNA from various donor microorganisms and combining portions of the DNA with the plasmid pUB110. Strains of *E. coli* or *B. subtilis* containing the recombinant DNA are grown in fermentation media to produce the amylase enzymes.

2 Claims, 4 Drawing Sheets

MUTANT MICROORGANISMS CONTAINING RECOMBINANT DNA AND THEIR USE IN THE PRODUCTION OF AMYLASES

FIELD OF THE INVENTION

The present invention relates to recombinant DNA comprising an amylase-coding gene and to microorganisms comprising the recombinant DNA and to their use in producing amylases.

BACKGROUND OF THE INVENTION

U.S. Pat. No. 4,469,791 discloses novel recombinant DNA containing an amylase-coding gene which is prepared by the in vitro process of cleaving DNA derived from a bacterial donor microorganism and combining the resulting DNA fragments with a vector, which has been similarly cleaved, the vector comprising a plasmid or the DNA of a derivative of phage lambda. This recombinant DNA may be inserted into a bacterial host organism and the latter cultivated to produce the amylase. A variety of bacterial donor and bacterial host organisms are described in the U.S. patent as are a number of suitable plasmids and derivatives of phage lambda.

The use of plasmids to introduce a gene into a microorganism is a widely-used technique. Recent literature contains descriptions of a number of plasmids which have been proposed for this purpose. In particular, two articles in "Gene", published by the Elsevier Biomedical Press, 15 (1981) 43–58, by Ilkka Palva, et al, and 19 (1982) 81–87, by Ilkka Palva alone, describe the isolation of the gene coding for alpha-amylase from *Bacillus amyloliquefaciens* by direct shotgun cloning using *B. subtilis* (*Bacillus subtilis*) as a host. The genome of *Bacillus amyloliquefaciens* was partially digested with the restriction endonuclease Mbo I, and 2- to 5-kb fragments were isolated and joined to plasmid pUB110. Competent *B. subtilis* amylase-negative cells were transformed with the hybrid plasmids and kanamycin-resistant transformants were screened for the production of alpha-amylase.

One of the problems of using a genetically-engineered microorganism on an industrial scale is the stability of the recombinant DNA which has been introduced by the genetic engineering process. If there is a lack of stability, the recombinant DNA tends to be lost or to undergo sequence rearrangements as successive generations of the organism are produced until eventually the amylase-coding gene is no longer or only weakly expressed by descendant microorganisms.

We have now developed recombinant DNA which comprises certain amylase-coding genes described in U.S. Pat. No. 4,469,791, but which is derived from a plasmid not specifically described in that patent. The plasmid is pUB110, whih was also described in an article in the Journal of Bacteriology 1978, Vol. 134, pp. 318–329. The plasmid pUB110 comprises a gene coding for resistance to kanamycin or to analogous antibiotics inactivated by the nucleotidyl transferase enzyme. We have found that the recombinant DNA derived from this plasmid and certain amylase-coding genes may be introduced into a host-microorganism and that, particularly when the host is *B. subtilis*, mutant strains may be produced and cultivated which have enhanced stability and high copy numbers. The mutant microorganisms which comprise the novel recombinant DNA may be used, therefore, on an industrial basis for the production of amylase and in particular, for the production of the alpha-amylase of *B. megaterium* (*Bacillus megaterium*), an amylase possessing particularly useful commercial properties.

SUMMARY OF THE INVENTION

In accordance with the present invention, there is provided, as a new composition of matter, recombinant DNA containing an amylase-coding gene prepared by the in vitro process of cleaving DNA derived from a donor microorganism and combining the resulting DNA fragments comprising the amylase-coding gene with a similarly cleaved vector which is a plasmid characterized in that the donor microorganism is a *Bacillus megaterium*, a *Bacillus coagulans*, a *Bacillus circulans*, a *Bacillus cereus*, or a *Klebsiella pneumoniae* and the plasmid is pUB110.

Further, in accordance with the present invention, there is provided a genetically-engineered microorganism containing recombinant DNA wherein the recombinant DNA comprises recombinant DNA containing an amylase-coding gene prepared by the in vitro process of cleaving DNA derived from a donor microorganism and combining the resulting DNA fragments comprising the amylase-coding gene with a similarly cleaved vector which is a plasmid characterized in that the donor microorganism is a *Bacillus megaterium*, a *Bacillus coagulans*, a *Bacillus circulans*, a *Bacillus cereus*, or a *Klebsiella pneumoniae* and the plasmid is pUB110.

In addition, in accordance with this invention, there is provided a process for producing an amylase enzyme by cultivating, under amylase-producing conditions, a genetically-engineered microorganism containing recombinant DNA wherein the recombinant DNA comprises recombinant DNA containing an amylase-coding gene prepared by the in vitro process of cleaving DNA derived from a donor microorganism and combining the resulting DNA fragments comprising the amylase-coding gene with a similarly cleaved vector which is a plasmid characterized in that the donor microorganism is a *Bacillus megaterium*, a *Bacillus coagulans*, a *Bacillus circulans*, a *Bacillus cereus*, or a *Klebsiella pneumoniae* and the plasmid is pUB110.

Figure 1:
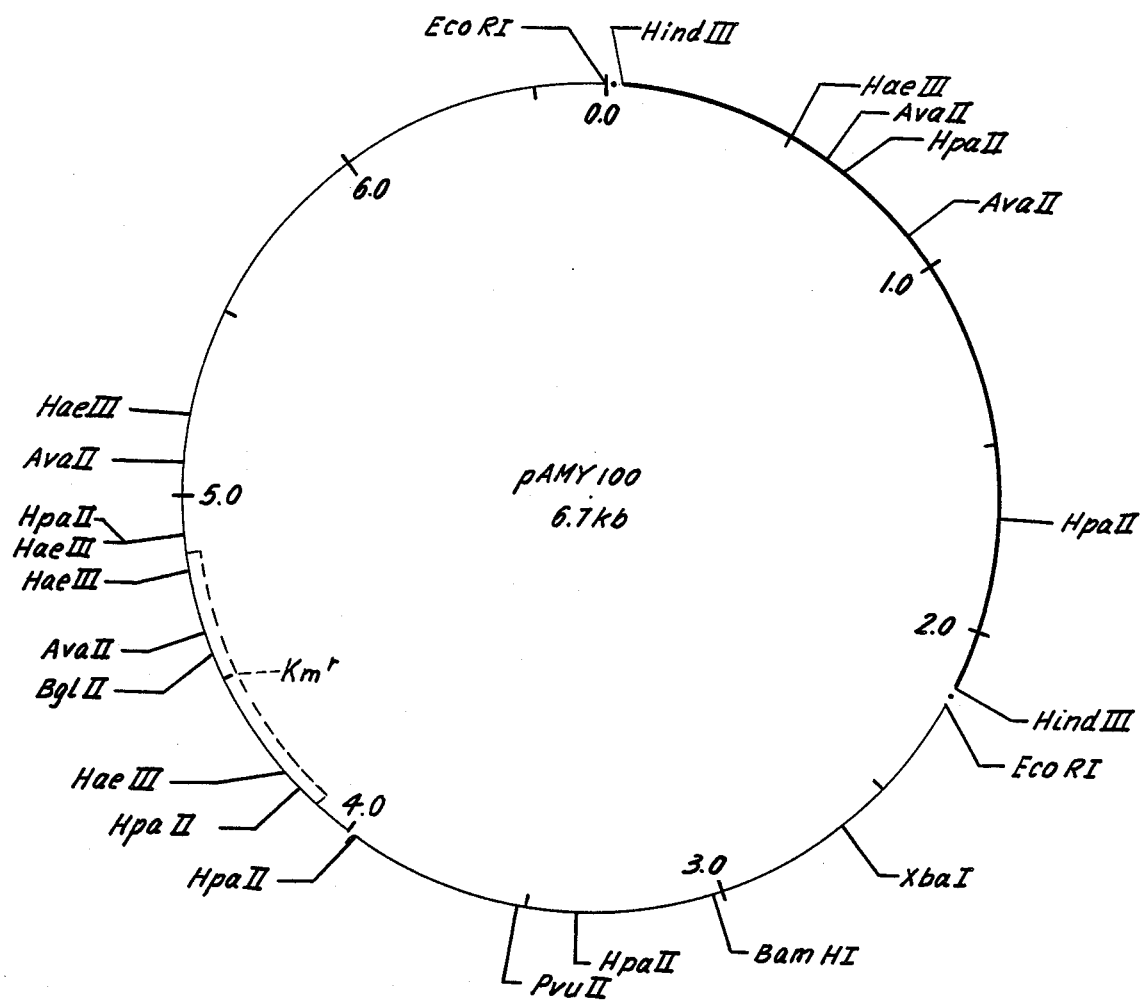
FIG. 1 is a map of the plasmid pAMY100 obtained by inserting a DNA fragment containing the alpha-amylase-coding gene from *B. megaterium* into pUB110.
Figure 2:
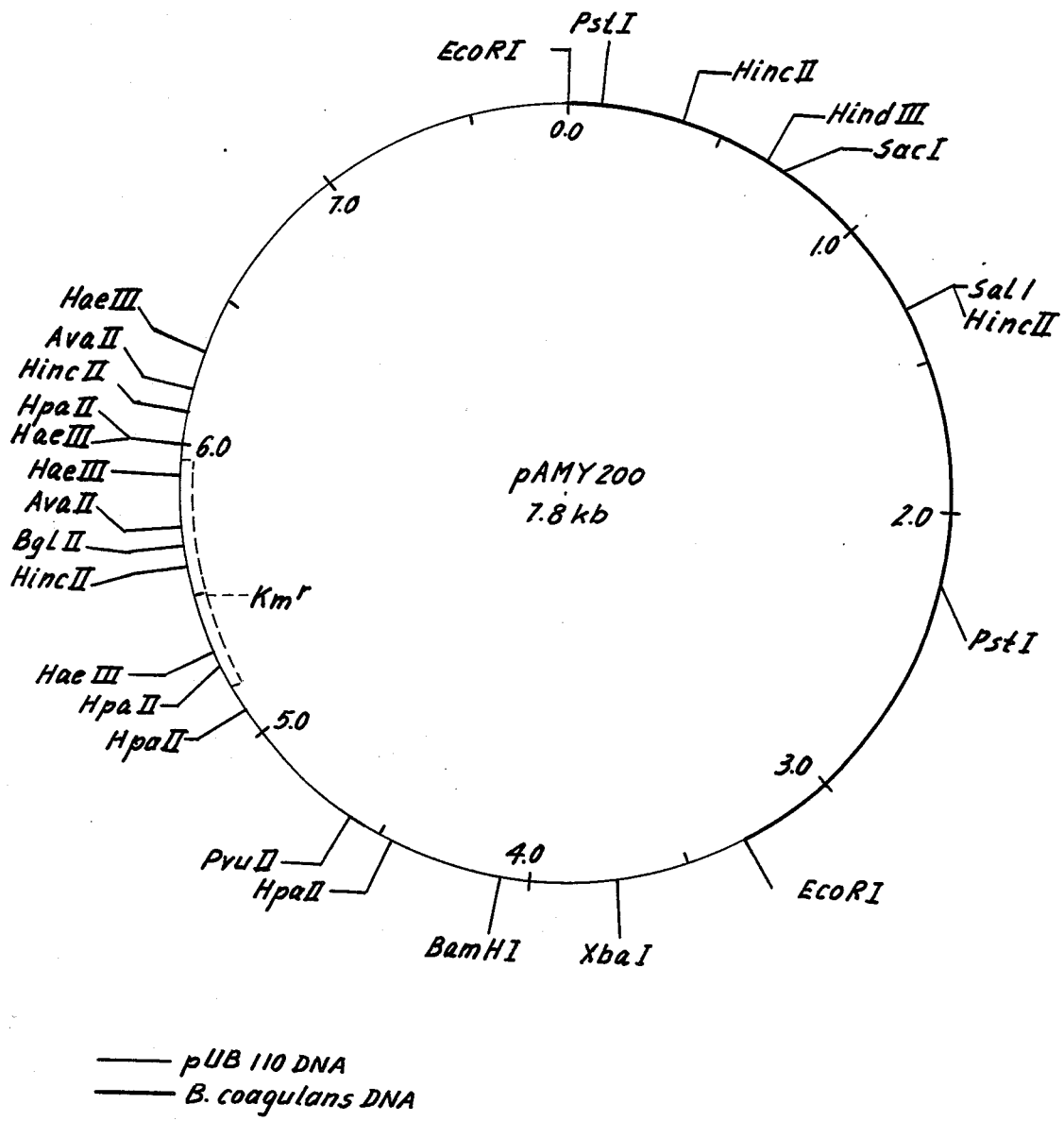
FIG. 2 is a map of the plasmid pAMY200 obtained by inserting a DNA fragment containing the alpha-amylase-coding gene from *B. coagulans* (*Bacillus coagulans*) into pUB110.
Figure 3:
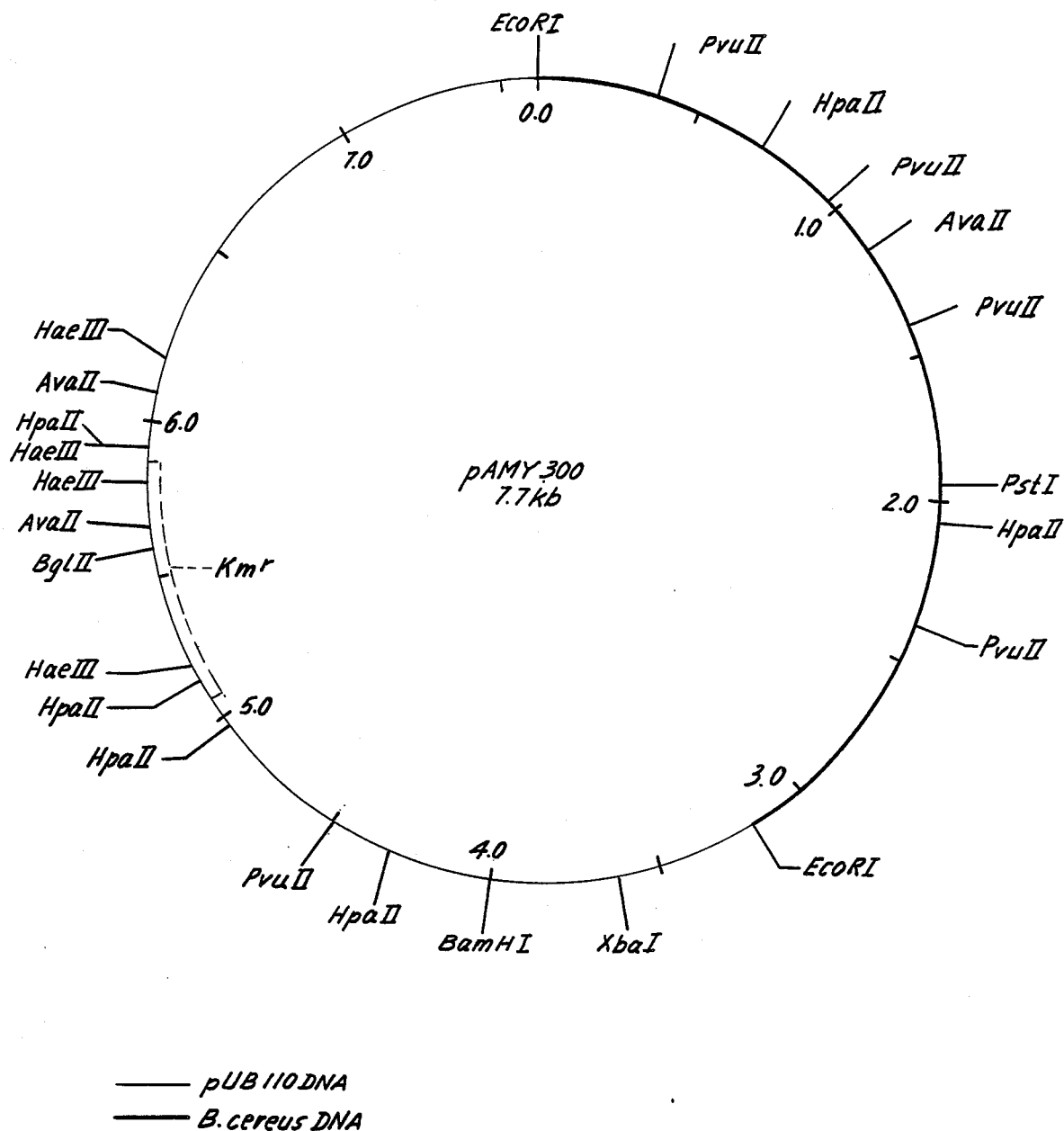
FIG. 3 is a map of the plasmid pAMY300 obtained by inserting a DNA fragment containing the beta-amylase-coding gene from *B. cereus* (*Bacillus cereus*) into pUB110.
Figure 4:
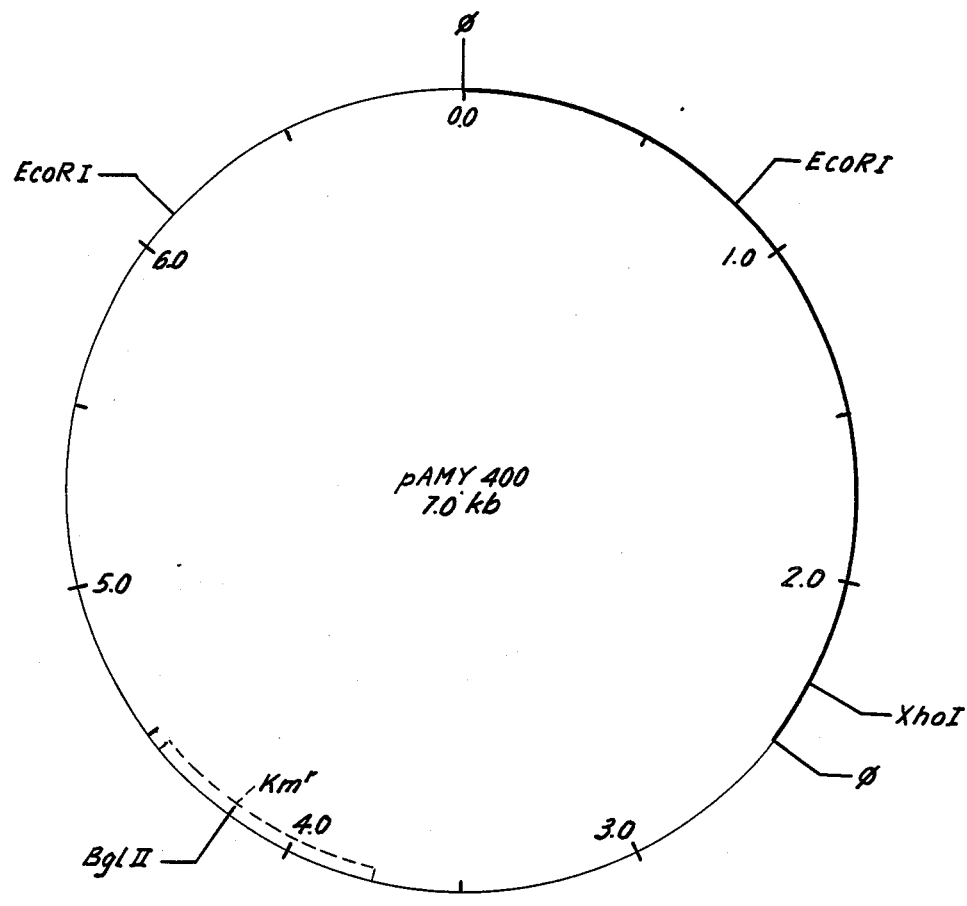
FIG. 4 is a map of the plasmid pAMY400 obtained by inserting a DNA fragment containing a beta-amylase-coding gene from *B. megaterium* into pUB110.

In all of the figures, the donor DNA is indicated by a heavy line.

DETAILED DESCRIPTION OF THE INVENTION

Specific useful donor microorganisms comprise *B. coagulans* NCIB No. 11571. The recombinant DNA produced from this donor and the cleaved vector pUB110 has been designated by us as pAMY200. Similarly, the recombinant DNA from *B. cereus* ATCC No. 31102 and the cleaved vector pUB110 has been designated by us as pAMY300. The microorganism B. megaterium NCIB No. 11568 contains genes coding for alpha-amylase and beta-amylase, respectively, and particularly useful recombinant DNA is that which arises from the combination of fragments of the DNA of *B. megaterium* NCIB No. 11568 comprising the gene coding for alpha-amylase and the cleaved vector pUB110 and which we have designated as pAMY100. The analogous recombinant DNA from the cleaved vector pUB110 and the fragment comprising the gene coding for beta-amylase we have designated as pAMY400. Another useful donor microorganism is *Klebsiella pneumoniae*, ATCC No. 15050, which contains a gene coding for pullulanase.

It should be pointed out that the term *B. megaterium* as used in this specification is intended to include accepted synonyms of *B. megaterium* including in particular *Bacillus carotarum* as described in Bergey's "Manual of Determinative Bacteriology" (eighth Edition) R. E. Buchanan and N. E. Gibbons, co-editors, p. 537.

The production of the recombinant DNA, according to the invention, is achieved by use of conventional and well-known techniques as described in the examples following later in this specification.

For industrial use, the recombinant DNA, according to the invention, is first incorporated into a host microorganism. The host may be a yeast or a bacterium, the latter being preferred. Although the recombinant DNA may be incorporated in any of the host bacteria described in U.S. Pat. No. 4,469,791, it is preferred to use a *B. subtilis*. Thus, the *B. subtilis* may be *B. subtilis* BGSC 1A289 or, more preferably, an asporogenic mutant of the latter which has been deposited as *B. subtilis* NCIB 11979 (hereinafter referred to as BAS8). When the latter is host for the recombinant DNA pAMY100, a new microorganism, Deposit No. *B. subtilis* NCIB 11980, is obtained (hereinafter referred to as BAS35).

In order to obtain improved stability and high copy number, it has been found that, by use of the following technique, BAS35 may be caused to mutate to give an organism in which these desirable properties are enhanced. The BAS35 is first grown on a nutrient medium which contains 250 micrograms/ml kanamycin or analogous antibiotic which may be inactivated by the nucleotidyl transferase enzyme. Some colonies are able to grow on this medium, others cannot, i.e., the former have higher kanamycin resistance. The colonies which have the capacity to grow on the medium are selected and are then cultivated separately. The selected strain has been found to be a mutant of BAS35 and has been deposited as *B. subtilis* NCIB 11984 (hereinafter referred to as BAS72). If, however, the new mutant strain is now transferred to a nutrient medium comprising 750 micrograms kanamycin/ml, a further selection may be made of a mutant capable of growing in this medium and hence being adapted to resist a concentration of 750 micrograms/ml of kanamycin. This mutant may be selected and grown separately and has been deposited as *B. subtilis* NCIB 11985 (hereinafter referred to as BAS73). Both the mutant strains, BAS72 and BAS73, besides possessing the kanamycin resistance, show enhanced stability and increased copy number. Thus, whereas the copy number of BAS35 is about 15, that of BAS72 is at least 25, and BAS73 at least 35.

This procedure may be used to produce mutant strains resistant to even higher concentrations of the antibiotic, e.g., up to 5000 micrograms/ml and with correspondingly higher copy numbers.

BAS72 and BAS73, with their stability and high plasmid copy numbers, are attractive for use industrially to prodce the alpha-amylase of *B. megaterium* NCIB No. 11568, since both contain the recombinant DNA, pAMY100, comprising the gene coding for this amylase. Similarly, starting with BAS8 or with *B. subtilis* BGSC 1A289, it is possible to introduce recombinant DNA according to the invention in which the amylase-coding gene is derived from other donors. For example, we have introduced the recombinant DNA pAMY200, pAMY300, and pAMY400 into BAS8 to give new microorganisms deposited as *B. subtilis* NCIB 11981 (hereinafter referred to as BAS36), *B. subtilis* NCIB 11982 (hereinafter referred to as BAS37), and *B. subtilis* NCIB 11983 (hereinafter referred to as BAS38), respectively.

These three strains may be mutated by the process described for the analogous BAS35 to give kanamycin-resistant mutants possessing increased stability and high copy numbers.

In order to make the high-copy-number mutant strains more suitable for industrial use, it is preferred to remove from the recombinant DNA contained in the respective microorganism the gene coding for kanamycin resistance. This may be accomplished by known genetic-engineering techniques, for example, techniques in which the recombinant DNA is removed from the microorganism, cleaved in vitro, and the gene coding for kanamycin resistance deleted therefrom by means of a restriction endonuclease. The resulting DNA is then ligated by means of a ligase and reinserted into a *B. subtilis* host, e.g., into BAS8 or into a "cured" form of BAS72 or BAS73.

Although the microorganisms containing the recombinant DNA, according to the invention, may be so engineered as to produce variety of amylases, they are of particular use in producing the alpha-amylase of *B. megaterium* NCIB No. 11568, which is an enzyme active in catalyzing the conversion of polysaccharides, such as starch and partial starch hydrolyzates as is described in our copending British Patent Application No. 8,414,272.

The invention will now be further described with reference to the following examples in which the following deposited strains and plasmids were employed:

*B. subtilis* BGSC 1A289: The organism is a mutant deficient in the gene coding for alpha-amylase. It was obtained from the Bacillus Genetic Stock Centre of Ohio State University.

pUB110: As described above.

pAMY1 (incorporated in *E. coli* [*Escherichia coli*] as Deposit No. NCIB 11570): A derivative of the E. coli plasmid pBR322 carrying a 2.2-kb Hind III insert with the alpha-amylase-coding gene of *B. megaterium* NCIB 11568. This plasmid is described in U.S. Pat. No. 4,469,791. pAMY2 (incorporated in *E. coli* as Deposit No. NCIB 11573): A derivative of the *E. coli* plasmid pBR322 carrying a 3.3-kb Eco RI insert with the alpha-amylase-coding gene of *B. coagulans* NCIB 11571. This plasmid is described in U.S. Pat. No. 4,469,791.

pAMY3 (incorporated in *E. coli* as Deposit No. NCIB 11602): A derivative of the *E. coli* plasmid pBR322 carrying a 3.2-kb Eco RI insert with the beta-amylase coding gene of *B. cereus* ATCC 31102. This plasmid is described in U.S. Pat. No. 4,469,791.

EXAMPLE 1 pAMY100: A recombinant plasmid derived from pUB110 and carrying a DNA segment coding for the alpha-amylase of *B. megaterium* NCIB 11568.

The donor DNA was pAMY1 and the in vitro recombination was performed between 1 microram of pAMY1 DNA and 2 micrograms of pUB110 DNA cleaved with 10 units of Eco RI restriction endonuclease. Ligation was performed at high concentration (75 micrograms DNA/ml) in the presence of 1 unit of $T_4$ DNA ligase, in order to generate concatemers.

The product obtained was used to transform BGSC 1A289 by the procedure described in "Experiments in Microbial Genetics", edited by Clowes and Highes, Blackwell 1968. Kanamycin-resistant and amylase-producing clones were identified in LB medium supplemented with 10 micrograms/ml of kanamycin and 1% starch, the amyase-producing clones being identified by iodine vapor by the procedure described in U.S. Pat. No. 4,469,791.

From the positive clones, there was selected a clone carrying pAMY100, a plasmid having retained the whole pUB110, the AMY fragment and only a small part of pBR322 limited by the Hind III sites flanking the AMY fragment.

pAMY100 DNA was then extracted from this strain and used to transform BAS8 as described in Example 5.

EXAMPLE 2 pAMY200: A recombinant plasmid derived from pUB110 and carrying a DNA segment coding for the alpha-amylase of *B. coagulans* NCIB 11571.

The in vitro recombination was carried out between pAMY2 DNA and pUB110 DNA by the procedure described in Example 1. pAMY200 was obtained as a 3.3-kb insert in the Eco RI site of pUB110. This plasmid (7.8 kb) was used to transform BAS8 as described in Example 8.

EXAMPLE 3 pAMY300: A recombinant plasmid derived from pUB110 and carrying a DNA segment coding for the beta-amylase gene of *B. cereus* ATCC 31102.

The donor was pAMY3 and the recombination was carried out by the procedure described in Example 1. pAMY300 was obtained as a 3.2-kb insert in the Eco RI site of pUB110. This plasmid was used to transform BAS8 as described in Example 9.

EXAMPLE 4

Preparation of *B. subtilis* BAS8, an Asporogenous Mutant of *B. subtili* BGSC 1A289

A sample of an overnight culture of BGSC 1A289 was irradiated with UV light and used to inoculate with successive subcultures the following medium:

| | |
|---|---|
| Difco Yeast Extract | 1 g |
| $MgSO_4.7H_2O$ | 200 mg |
| $FeSO_4.7H_2O$ | 10 mg |
| $MnSO_4.H_2O$ | 7 mg |
| $CaCl_2.2H_2O$ | 73 mg |
| $PO_4$ Buffer pH 7.0 | 0.067 M |
| Glutamate | 0.1 M |
| Methionine | 40 mg |
| Aromatic Amino Acids | 40 mg |
| $H_2O$ | 1 l |

This medium is described by Bergere and Hermier (Ann. Inst. Pasteur 106, 214–235, 1964) as a sporulation-inducing medium. Successive subcultures in such a medium give a selective advantage to the vegetative cells (which fail to sporulate) versus the spores which must first germinate before being able to proliferate. Thus, each subculturing step can enrich the population in asporogenous mutants. BAS8 was isolated after six subcultures.

The genetic markers reported for *B. subtilis* BGSC 1A289 are:

amyE: A mutation in the structural gene coding for the alpha-amylase of *B. subtilis* resulting in the absence of the alpha-amylase.

aroI906: A mutation in the structural gene coding for the shikimate kinase resulting in a requirement (auxotrophy) for the aromatic amino-acids (phenylalanine, tyrosine and tryptophan).

metB5: A mutation in the structural gene coding for one of th enzymes of the methionine biosynthetic pathway resulting in a requirement for methionine.

sacA321: A mutation in a structural gene coding for an enzyme involved in sucrose catabolism and resulting in the inability to catabolize sucrose.

The effect of the ultraviolet treatment was to produce a mutation in an unknown gene resulting in the inability to sporulate. The mutant BAS8 produces less than one spore for $10^7$ bacteria in the sporulation medium described above, while *B. subtilis* BGSC 1A289 produces one spore for two bacteria under the same conditions. The mutant organism *B. subtilis* BAS8 contains the genetic marker spo8 but at the same time has lost the markers aroI906 and sacA321 during the mutation process.

EXAMPLE 5

Preparation of BAS35 Containing the Recombinant DNA pAMY100 pAMY100 DNA was used to transform BAS8 by the method referred to in Example 1 and described in "Experiments in Microbial Genetics" referred to above.

The plasmid stability of BAS35 was measured by successive subculturing at 37° C. in a complete medium (Difco tryptone, 1%; Difco yeast extract, 1%., NaCl, 0.5%) without kanamycin, the antibiotic to which plasmid pUB110 confers resistance. (Material bearing the Difco trademark is available from the Difco Laboratories, Detroit, Mich.)

A first subculture was inoculated with a sample of an overnight culture grown in the presence of 20 micrograms/ml of kanamycin. For each subculture, a viable count was done immediately after inoculation and after growth in order to determine the number of generations. The generation time of BAS35 in exponential phase in complete medium at 37° C. is 30 minutes.

After each subculture, the percentage of amylase-positive clones (having retained the plasmid) was measured. The results were as follows:

| Number of Generations | Percent of Amy+ Clones |
|---|---|
| 10 | 100 |
| 19 | 100 |
| 29 | 90.7 |
| 35 | 58.7 |
| 46 | 14.4 |

| Number of Generations | Percent of Amy+ Clones |
|---|---|
| 53 | 4.9 |

EXAMPLE 6

Production of BAS72, a Mutant of BAS35, and Which Comprises a Mutation in an Unknown Gene Which Codes for Increased Kanamycin Resistance and Plasmid Stability BAS35, containing the plasmid pAMY100 which confers resistance to kanamycin at a maximum concentration of about micrograms/ml, was grown overnight in complete medium. Without mutagenic treatment, samples of 0.1 ml were spread onto plates containing complete medium and supplemented with micrograms/ml of kanamycin. After 2 days of incubation at 37° C., clones resistant to this concentration of kanamycin arose at a frequency of $10^{-6}$ per inoculated BAS35 cell. One clone, designated BAS72, was chosen from the resistant clones and the mutation conferring the increased resistance to kanamycin phenotype was designated irk72. This phenotype maintained its stability after several subcultures in the absence of the antibiotic. The generation time of BAS72 in exponential phase in complete medium at 37° C. is 60 minutes.

Stability of pAMY100 in BAS72

Stability was measured as in the case of BAS35 and is reported below. It is clear that pAMY100 is much more stable in BAS72 than in BAS35.

| Number of Generations | Percent of Amy+ Clones |
|---|---|
| 11 | 100 |
| 17 | 100 |
| 29 | 100 |
| 34 | 100 |
| 45 | 100 |
| 50 | 100 |

EXAMPLE 7

Production of BAS73 Comprising a Mutation of an Unknown Gene Conferring a Higher Resistance to Kanamycin Than in the Previous Example A sample of 0.1 ml of an overnight culture in complete medium of BAS72 (which is resistant to kanamycin at a concentration of 250 micrograms per ml) was spread on a plate containing complete medium supplemented with 750 micrograms/ml of kanamycin. Clones spontaneously resistant at this concentration of the antibiotic arose at a frequency of $10^{-6}$ per plated cell. One such clone was purified and designated as BAS73. Its resistance to 750 micrograms/ml of kanamycin was maintained in stability after several subcultures in the absence of the antibiotic.

The generation time of BAS73 in exponential phase in complete medium at 37° C. is 60 minutes.

Stability of pAMY100 in BAS73

Plasmid stability was measured as in the case of BAS35 and is reported below. It is clear that pAMY100 is much more stable in BAS73 than in BAS35.

| Number of Generations | Percent of Amy+ Clones |
|---|---|
| 10 | 100 |
| 18 | 100 |
| 28 | 100 |
| 34 | 100 |
| 45 | 100 |
| 50 | 100 |

EXAMPLE 8

Preparation of BAS36 Containing the Recombinant DNA pAMY200 pAMY200 DNA was used to transform BAS8 by the method referred to in Example 1 and described in "Experiments in Microbial Genetics" referred to above.

The plasmid stability was measured in the same way as that of pAMY100 in BAS35.

Results are given below:

| Number of Generations | Percent of Amy+ Clones |
|---|---|
| 20 | 17.6 |
| 36 | 5.8 |
| 52 | 0.4 |

EXAMPLE 9

Preparation of BAS37 Containing the Recombinant DNA pAMY300 pAMY300 DNA was used to transform BAS8 by the method referred to in Example 1 and described in "Experiments in Microbial Genetics" referred to above.

Plasmid stability was measured in the same way as that of pAMY100 in BAS35.

Results are given below:

| Number of Generations | Percent of Amy+ Clones |
|---|---|
| 10 | 100 |
| 26 | 100 |
| 44 | 100 |
| 55 | 96 |

EXAMPLE 10 pAMY400: A recombinant plasmid derived from pUB110 and carrying a DNA segment coding for the beta-amylase gene of B. megaterium NCIB 11568.

The gene which codes for the beta-amylase of B. megaterium NCIB 11568 was first cloned in E. coli by means of phage lambda before being subcloned in E. coli plasmid pBR322 to produce a new, recombinant plasmid pAMY4 (deposited in E. coli HB101 as NCIB 11986). The latter was then used to introduce the beta-amylase-coding gene into pUB110. The procedure was as follows.

Cloning of DNA of B. megaterium NCIB 11568 in Phage Lambda

Two micrograms of B. megaterium NCIB 11568 total DNA were cleaved with 10 units of restriction endonuclease Hind III at 37° C. for 2 hours; about 1 microgram of phage lambda NM590 was simultaneously cut with the same enzyme. The two digested DNAs were mixed and incubated for 6 hours at 12° C. with 1 unit T4 DNA ligase to allow reannealing and covalent binding of the cohesive ends of the DNA fragments.

This ligation mixture was added to an in vitro encapsidation preparation of phage lambda and the encapsidated DNA was incubated with *E. coli* HB101 cells for infection and spread on starch agar medium. Seventy percent of the plaques formed contained recombinant molecules.

After exposing the plates to iodine vapor, plaques surrounded by a white area were found at a frequency of 1 on 800 recombinant plaques; one was picked and called lambda NM950 beta-amyl. After its DNA restriction, an insertion of a 5-kb Hind III fragment was observed.

Subcloning of the beta-Amylase Gene in *E. coli* pBR322 Plasmid

One microgram of the DNA of lambda NM590 beta-amyl and 0.6 microgram of pBR322 DNA were cleaved with Hind III, mixed and treated with T4 DNA ligase.

The ligation mixture was used to transform *E. coli* HB101 competent cells, selected for ampicillin resistance and screening for tetracycline sensitivity and amylase production.

One type of Amy+ plasmid was found at a frequency of 6%; the pBR322 plus an insertion of 5-kb Hind III foreign fragment, containing the beta-amylase gene from *B. megaterium* NCIB 11568. This plasmid was called pAMY4.

Subcloning of the beta-Amylase Gene in *B. subtilis* pUB110 Plasmid

The unavailability of a Hind III restriction site necessitated the identification of other sites on both sides of the beta-amylase gene to allow the subcloning in pUB110. After a detailed restriction mapping, two Bgl II sites were found in the 5-kb foreign fragment surrounding 2.5-kb pairs. This size site could contain an active beta-amylase gene. Moreover, the Bgl II cohesive ends could join with Bam HI ends (pUB110 has a unique restriction site for the latter).

Two micrograms of pUB110 were cut with Bam HI and 1 microgram of pAMY4 was cut with Bgl II and Hind III. The fragments were annealed in the presence of 1 unit T4 DNA ligase. After transformation by the method described in Example 1, one type of Amy+ recombinant plasmid was found in *B. subtilis*. The new plasmid contains 2.5-kb insert in the Bam HI site of pUB110. This 7-kb plasmid was called pAMY400 and was introduced in BAS8 to generate BAS38.

EXAMPLE 11

Production of alpha-Amylase by *B. subtilis* BAS35 and BAS73

Four 20-liter fermentors containing 15 liters culture medium comprising, by weight to volume, 1% bactopeptone, 3% yeast extract, 0.5% glucose, and 0.5% NaCl were inoculated with 1% of a preculture contained in the same medium. The precultures were prepared by making several subcultures so that, in the final stage before the fermentors, about 35 generations had been produced. Two fermentors were seeded with the strain BAS35 in the presence and absence of kanamycin (5 micrograms/ml) and two with the strain BAS73 in the presence and absence of kanamycin (5 micrograms/ml). The fermentors were agitated at 250 rpm, aerated at 0.15 liter air/liter/minute and kept at 40° C. for 55 hours. After 6 hours and for a further period of 48 hours, the fermentors were fed continuously with a glucose solution so that the total glucose added to the fermentors was 1.5% (w/v). At the end of the fermentation, the alpha-amylase activity was measured in the culture broth.

The amylase activity of a given sample is determined by the PHADEBAS test which employs a commercially available test kit and which is based on the optical estimation of the strength of a dye liberated by the enzyme under carefully controlled conditions. If the activity of the enzyme is completely unknown, samples are first diluted with water to produce a range of dilutions which are then tested by the method described below to find the dilution which, under the test conditions, gives an optical density of the dye in the range suitable for quantitative determination. The test is then repeated at this concentration in comparison with a blank sample.

In detail, 200 microliters of diluted enzyme sample is placed in a test tube and mixed with 4 ml of buffer solution. The blank consists of 200 microliters demineralized water and 4 ml buffer solution. The buffer solution comprises sodium acetate (20 mM) and calcium chloride (2 mM) adjusted to pH 5. A PHADEBAS tablet, Pharmacia Diagnostics, Piscataway, N.J., is then added to each sample, the sample agitated for 10 seconds, and the sample placed in a well-stirred water bath where it is held at 55° C. for 15 minutes. The PHADEBAS tablet contains a dye and a buffer, the effect of the two buffer systems being to establish a final pH of 6.3 in the test solution.

After the 15-minute period, the reaction is stopped by adding 1 ml of 0.5 molar sodium hydroxide and the sample agitated before being centrifuged at approximately 1500 g for 5 minutes or filtered. The absorbance of the sample is then measured at 620 nm against demineralized water using a cuvette of 1-cm light path. The absorbance of the blank is subtracted from the sample under test and the amylase activity determined in units/ml from the PHADEBAS standard curve.

The results are shown in the following table:

|  | Enzyme Activity (units/ml) | |
| --- | --- | --- |
|  | BAS35 | BAS73 |
| Fermentor with Kanamycin | 220 | 160 |
| Fermentor without Kanamycin | 80 | 150 |

Thus, there has been provided, in accordance with this invention, recombinant DNA containing amylase-coding genes and microorganisms containing the recombinant DNA. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A kanamycin-resistant mutant of a genetically-engineered *Bacillus subtilis* microorganism containing recombinant DNA wherein the recombinant DNA comprises plasmid pAMY100 having a molecular weight of approximately 6.7 kb and a restriction endonuclease cleavage map as shown in FIG. 1, said microorganism being capable of growing in a nutrient medium containing at least 250 micrograms kanamycin/ml and having the Deposit No. *Bacillus subtilis* NCIB 11984 (BAS 72).

2. A kanamycin-resistant mutant of the *Bacillus subtilis* microorganism of claim 1 capable of growing in a nutrient medium containing at least 750 micrograms kanamycin/ml and having the Deposit No. *Bacillus subtilis* NCIB 11985 (BAS73).

* * * * *